United States Patent [19]

Smith, Jr. et al.

[11] Patent Number: 5,003,124
[45] Date of Patent: Mar. 26, 1991

[54] OLIGOMERIZATION PROCESS

[75] Inventors: Lawrence A. Smith, Jr., Bellaire; Dennis hearn, Houston; Edward M. Jones, Jr., Friendswood, all of Tex.

[73] Assignee: Chemical Research & Licensing Company, Houston, Tex.

[21] Appl. No.: 268,074

[22] Filed: Oct. 31, 1988

Related U.S. Application Data

[60] Division of Ser. No. 58,698, Jun. 1, 1987, which is a continuation of Ser. No. 442,359, Nov. 17, 1982, abandoned.

[51] Int. Cl.$^5$ .............................................. C07C 2/02
[52] U.S. Cl. ..................... 585/526; 585/520; 585/527
[58] Field of Search ................. 585/520, 526, 527

[56] References Cited

U.S. PATENT DOCUMENTS

| | | | |
|---|---|---|---|
| 2,373,501 | 4/1945 | Peterson | 260/667 |
| 2,670,393 | 2/1954 | Howerton | 585/526 |
| 3,121,124 | 2/1964 | Verdal | 568/697 |
| 3,629,478 | 12/1971 | Haunschild | 260/677 |
| 3,634,534 | 1/1972 | Haunschild | 260/677 |
| 3,825,603 | 7/1974 | Maisie | 260/612 D |
| 3,846,088 | 11/1974 | Brown | 44/56 |
| 4,071,567 | 1/1978 | Anallotti et al. | 260/614 |
| 4,198,530 | 4/1980 | Weinztheimer | 568/697 |
| 4,215,011 | 7/1980 | Smith | 252/426 |
| 4,232,177 | 11/1980 | Smith | 585/324 |
| 4,242,530 | 12/1980 | Smith | 585/510 |
| 4,250,052 | 2/1981 | Smith | 252/426 |
| 4,302,356 | 11/1981 | Smith | 252/421 |
| 4,307,254 | 12/1981 | Smith | 568/697 |
| 4,336,407 | 6/1982 | Smith | 568/697 |

FOREIGN PATENT DOCUMENTS

| | | | |
|---|---|---|---|
| 0737535 | 6/1966 | Canada | 585/526 |
| 056379 | 7/1973 | Canada | 260/695 |
| 0734498 | 8/1955 | United Kingdom | 585/520 |

OTHER PUBLICATIONS

Derrier, M. L., et al., "The IFP Selective Hydrogenation Process", *Chemical Engineering Progress*, vol. 70, No. 1, Jan. 1974, pp. 74–80.

Scheeline & Terada-Process Economic Reviews SRI International, Menlo Park, Calif.

*Primary Examiner*—Patrick P. Garvin
*Assistant Examiner*—E. D. Irzinsiu
*Attorney, Agent, or Firm*—Kenneth H. Johnson

[57] ABSTRACT

A liquid phase process for oligomerization of $C_4$ and $C_5$ isoolefins or the etherification thereof with $C_1$ to $C_6$ alcohols wherein the reactants are contacted in a reactor with a fixed bed acid cation exchange resin catalyst at an LHSV of 5 to 20, pressure of 0 to 400 psig and temperature of 120 to 300° F. wherein the improvement is the operation of the reactor at a pressure to maintain the reaction mixture at its boiling point whereby at least a portion but less than all of the reaction mixture is vaporized. By operating at the boiling point and allowing a portion of the reaction mixture to vaporize, the exothermic heat of reaction is dissipated by the formation of more boil up and the temperature in the reactor is controlled.

11 Claims, 1 Drawing Sheet

OLIGOMERIZATION PROCESS

The Government of the United States of America has certain rights in this invention pursuant to Contract No. DOE-FC07-800CS40454, awarded by the U.S. Department of Energy.

This application is a divisional of Ser. No. 058,698, filed Jun. 1, 1987 which is continuation of Ser. No. 442,359 filed Nov. 17, 1982, now abandoned.

BACKGROUND OF THE INVENTION

1. Field of the Invention

The present invention relates to an improved process for carrying out liquid phase oligomerizations and etherifications in a fixed catalyst bed.

2. Related Art

Recently a new method of conducting certain catalytic reactions has been devised. Two particular reactions for which this method has been particularly useful are oligomerization and etherification of $C_4$ and $C_5$ isoolefins. The method involved is briefly described as one where concurrent reaction and distillation occur in a combination reactor-distillation column with the distillation structure serving as the catalyst. This process and catalytic distillation structures are described in several U.S. Pat. Nos., namely U.S. Pat. Nos. 4,242,530; 4,250,052; 4,232,177; 4,302,356; 4,307,254; and 4,336,407.

This new system has been commercially applied to the production of methyl tertiary butyl ether (MTBE) produced by the reaction of isobutene contained in $C_4$ refinery streams and methanol.

It is well known that primary alcohols will react preferentially with the tertiary alkenes in the presence of an acid catalyst, for example, as taught in U.S. Pat. Nos. 3,121,124; 3,629,478; 3,634,534; 3,825,603; 3,846,088; 4,071,567; and 4,198,530.

The catalytic distillation process differs from these older processes in that a catalyst system was disclosed (U.S. Pat. Nos. 4,215,011 and 4,302,356) which provided for both reaction and distillation concurrently in the same reactor, at least in part within the catalyst system. For example, in this system and procedure, methanol and an isobutene containing $C_4$ stream are continuously fed to the reactor/distillation column where they are contacted in the catalytic distillation structure. The methanol preferentially reacts with isobutene, forming MTBE, which is heavier than the $C_4$ components of the feed and the methanol, hence it drops in the column to form the bottoms. Concurrently, the unreacted $C_4$'s (e.g. n-butane, n-butenes) are lighter and form an overhead.

The reaction just described is reversible, which means that it is normally equilibrium limited, however, by removing the ether (MTBE) from contact with the catalyst (as a bottoms), the reaction is forced to completion (Le Chatelier Principle). Hence it can be run to obtain a very high conversion of the isobutene present (95%+). As a result, a great deal of control over the rate of reaction and distribution of products can be achieved by regulating the system pressure. The boiling point in the reactor is determined by the boiling point of the lowest boiling material (which could be an azeotrope) therein at any given pressure. Thus at a constant pressure a change in the temperature at a point within the column indicates a change in the composition of the material at that point. Thus to change the temperature in the column the pressure is changed for any given composition.

Since oligomerization and etherification are exothermic there is excess heat in the reactor. In the liquid phase system, methods were devised to remove this heat, since in the case of resin type catalysts excessive temperature (hot spots) can damage the catalyst. In the catalytic distillation the excess heat merely causes more boil up in the column.

In an unrelated area the volatilization of a portion of the feed in a catalytic $C_3$ hydrogenation to provide a quasiisothermal reactor is discussed in *Chemical Engineering Progress*, Vol 70, No. 1, January, 1974, pages 74–80.

In addition to the catalytic distillation system, there are several other etherification systems in commercial use or available which are liquid phase systems That is, these systems are operated under conditions of pressure to maintain the contents of the reactor in liquid phase. One other principal problems encountered in these systems is the exothermic heat of reaction. Heat is sometimes removed by using heat exchangers in the reactor, such as tubular reactors having a heat exchange medium contacting the tubes, other systems employ feed diluents to maintain a low concentration of reactive isobutene. In other words, the temperature in the catalyst bed has to be controlled by the removal of excess heat in some manner.

The present invention which relates to the liquid phase type of reaction also provides a means for removing heat from the fixed continuous catalyst bed. It is a further advantage that the present type of liquid phase reaction may be used in conjunction with a catalytic distillation column reactor to obtain very high conversions of iso $C_4$ and $C_5$ alkenes in the feed stream.

These and other advantages will become apparent from the following descriptions.

SUMMARY OF THE INVENTION

The present invention is an improvement in the exothermic, liquid phase reaction of $C_4$ and $C_5$ isoolefins with themselves to form oligomers, preferably dimers, and with $C_1$ to $C_6$ alcohol to form ethers by contact in a fixed bed catalyst of acidic cation exchange resin, wherein the improvement is the operation of the reactor at a pressure to maintain the reaction mixture at its boiling point within the range of 120 degrees F. to 300 degrees F. whereby at least a portion but less than all of said reaction mixture is in the vapor phase.

This is a substantial departure from the prior art for this type of reactor, where sufficient pressure was employed to maintain the reaction mixture in liquid phase.

A given composition, the reaction mixture, will have a different boiling point at different pressures, hence the temperature in the reactor is controlled by adjusting the pressure to the desired temperature within the recited range. The boiling point of reaction mixture thus is the temperature of the reaction and the exothermic heat of reaction is dissipated by vaporization of the reaction mixture. The maximum temperature of any heated liquid composition will be the boiling point of the composition at a given pressure, with additional heat merely causing more boil up. The same principal operates in the present invention to control the temperature. There must be liquid present, however, to provide the boil up, otherwise the temperature in the reactor will continue to rise until the catalyst is damaged. In order to avoid exotherms which will vaporize all of the reaction mixture, it is necessary to limit the amount of isoolefin in the feed to the reactor to about 60 wt.% of the total feed.

The present reaction can be used on streams containing small amounts of the isoolefin, however, feed to the reaction will need to be preheated to near the boiling point of the reaction mixture, since low concentrations of isoolefin (1 to 8 wt. %) do not provide a very great exotherm (i.e., as noted above the prior art used diluents to control the temperature in the liquid phase reaction). In any event it may be necessary to preheat the feed to the reaction such that temperature of the reaction, i.e., the boiling point of the reaction mixture (feed temperature plus exotherm) is in the range of 120° F. to 300° F., which represents the desirable range for the equilibrium reactions at a pressure in the range of 0 to 400 psig.

The catalyst bed may be described as a fixed continuous bed, that is, the catalyst is loaded into the reactor in its particulate form to fill the reactor or reaction zone, although there may be one or more such continuous beds in a reactor, separated by spaces devoid of catalyst.

DETAILED DESCRIPTION OF THE INVENTION

Figure 2:
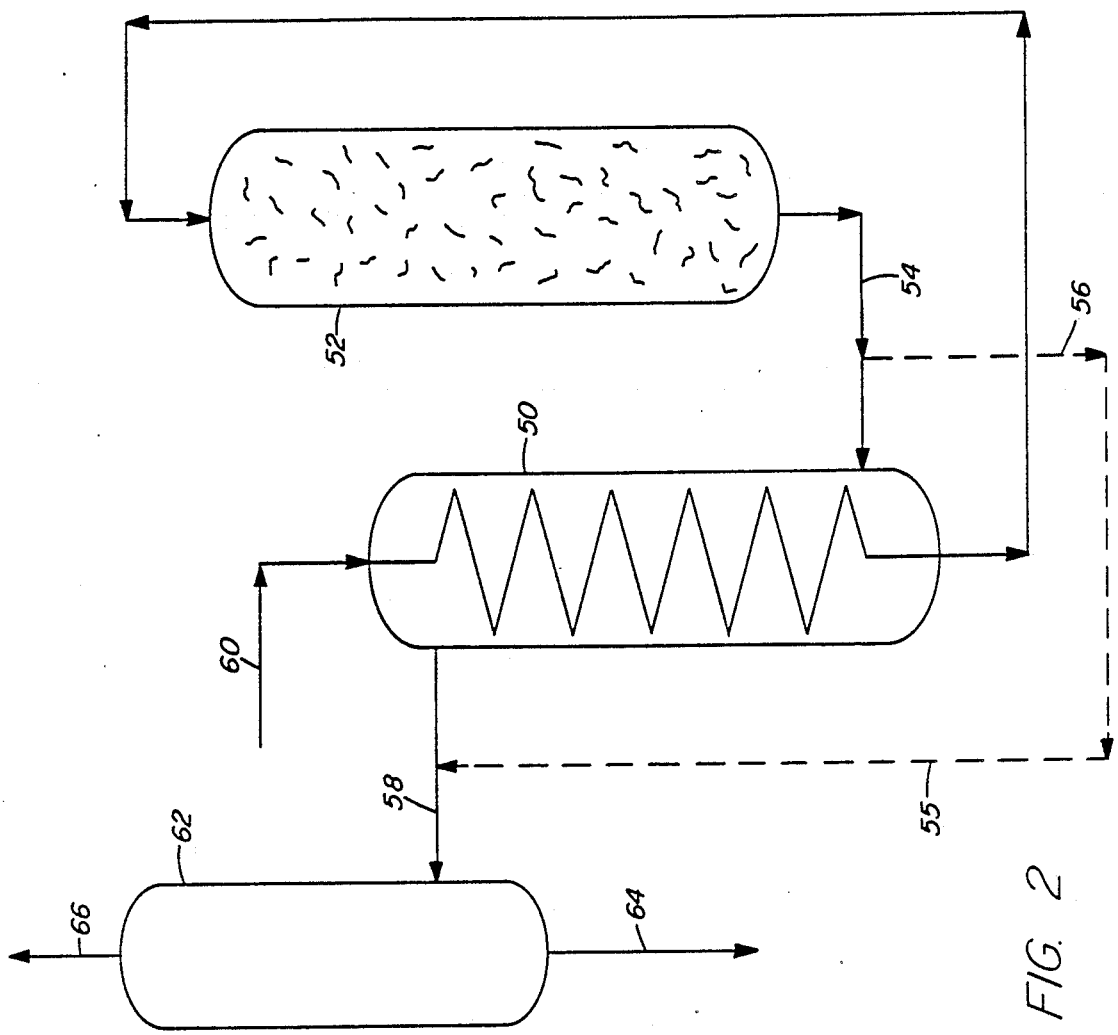
FIG. 2 is a modification where the heat of the reaction is recovered to preheat the feed to the reactor, i.e., operated quasi-isothermally and adiabatically.

The temperature in the reactor is thus controlled by the pressure used. The temperature in the reactor and catalyst bed is limited to the boiling point of the mixture present at the pressure applied, notwithstanding the magnitude of the exotherm. A small exotherm may cause only a few percent of the liquid in the reactor to vaporize whereas a large exotherm may cause 30-90% of the liquids to vaporize. The temperature, however, is not dependent on the amount of material vaporized but the composition of the material being vaporized at a given pressure. That "excess" heat of reaction merely causes a greater boil up (vaporization) of the material present.

Although the reaction is exothermic, it is necessary to initiate the reaction, e.g., by heating the feed to the reactor. In prior reactors such as the tubular reactors the temperature of the temperature of the reaction (bed) may be controlled with the heat exchange medium; i.e., either adding or removing heat or removing heat as required. In any event once the reaction is initiated an exotherm develops and must be controlled to prevent a runaway reaction or damage to the catalyst.

The reaction product (ethers, dimers, unreacted feed) in the present invention is at a higher temperature than the feed into the reactor with a portion being vapor and a portion liquid. The reactor is operated at a high liquid hourly space velocity (5-20 LHSV, preferably 10-20) to avoid the reverse reaction and polymerization of the olefins present in the feed). Under these conditions high conversion of feeds, containing 5 to 30 weight percent isoolefins are obtained, e.g., 80-90% conversion and somewhat lower conversions for stream containing higher concentrations of the isoolefins.

Thus, it may be desirable to have two and possibly more of the present reactors in series to obtain higher conversions of the isoolefins. In such a case the product from the first reactor will normally be cooled, by heat exchange to obtain the desired temperature in the second reactor.

Conveniently the feed to the first reactor is used to cool the product from the first reactor prior to its entry into the second reactor, hence the heat of reaction supplies some of the heat necessary to initiate the reaction in the first reactor. This method of recovering the heat of reaction can also be used where a single reactor is employed. Hence the reactor, or reactors can be operated in a substantially adiabatic manner.

The product from either a single reactor or a series of reactors operated quasi-isothermally as taught here may be separated by conventional distillation, by recovering oligomer or the ether as a bottom product and unreacted feed components as overheads, with appropriate water washing to remove or recover any alcohol (methanol and ethanol form azeotropes with the unreacted $C_4$ and $C_5$ feed stream components).

However, a further embodiment of the present invention is the combination of the present reaction operated in fixed bed in partial liquid phase (as described) with a catalytic distillation using an acidic cation exchange resin as the distillation structure. This has the advantage of further reacting the residual isoolefins while fractionating the reaction product concurrently to produce even higher conversion of the isoolefins. This combination has a further advantage in that both catalyst beds, i.e., the fixed partial liquid phase reactor and the catalytic distillation reactor can be relatively small compared to the use of either bed alone when used to obtain the same level of isoolefin conversion obtained by the combination.

Another advantage of the combination is that the small partial liquid phase bed can serve as a guard bed for the distillation column reactor bed, since catalyst poisons (metal ions and amines) even if present in parts per billion will deactivate the acidic cation exchange resin in time. The small guard bed can be easily and less expensively replaced as it is deactivated while the life of the catalytic distillation bed may be extended several years.

Catalysts suitable for the present process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g. U.S. Pat. No. 2,366,007). Further sulfonic acids group may be introduced into these polymers which already contain sulfonic acid groups; for example, by treatment with fuming sulfuric acid, i.e., sulfuric acid which contains sulfur trioxide The treatment with fuming sulfuric acid is preferably carried out at 0° to 150° C. and the sulfuric acid should contain sufficient sulfur trioxide after the reaction so that it still contains 10 to 50% free sulfur trioxide.

The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent specification 908,247).

The ion exchange resin is preferably used in a granular size of about 0.25 to 1 mm, although particles form 0.15 mm up to about 1 mm may be employed. The finer catalysts provide high surface area, but also result in high pressure drops throughout the reactor. The macroreticular form of these catalysts is preferred because of the much larger surface area expose and the limited swelling which all of these resins undergo in a non-aqueous hydrocarbon medium.

Similarly, other acid resins are suitable, such as perfluorosulfonic acid resins which are copolymers of sulfonyl fluorovinyl ethyl and fluorocarbon and described in greater detail in DuPont "Innovation", volume 4, No. 3, Spring 1973 or the modified forms thereof as described in U.S. Pat. Nos. 3,784,399; 3,770,567 and 3,849,243.

The resin catalyst is loaded into a reactor as a fixed bed of the granules. The feed to the reaction is fed to the bed in liquid phase. The bed may be horizontal, vertical or angled. Preferably the bed is vertical with the feed passing downward through the bed and exiting, after reaction, through the lower end of the reactor.

For the present oligomerization and etherification reactions, the feed may be a $C_4$ or $C_5$ containing stream, for example, a $C_4$ or $C_5$ refinery cut, although a mixed stream could be employed. In addition to $C_4$, such a $C_4$ stream may contain small amounts of $C_3$ and $C_5$ and a $C_5$ will contain small amounts of $C_4$ and $C_6$, depending on the precision of the refinery fractionation.

Isobutene is the $C_4$ isoolefin and it dimerizes to produce diisobutene. Some higher oligomers are produced as well as some codimers with n-butenes that are normally present in a $C_4$. The dimerization is the preferential reaction because the two most reactive molecules are combining. Higher polymers result from the continued contact of the dimer with isobutene in the presence of the catalyst. At the high LHSV (low residence time) employed for the present reaction, little polymer is formed.

Isoamylene has two isomers, i.e., 2-methyl butene-1 and 2 methyl butene-2, both of which are normally present in a $C_5$ stream. Both are highly reactive and the dimer product is a mixture of the three possible dimers.

Both the isobutene and isoamylene preferentially react with alcohols in the presence of an acid catalyst, hence only small amounts of dimer or other oligomerization products are produced when the etherification is carried out.

The $C_1$ to $C_6$ alcohol for the etherification may be fed to the reactor with the hydrocarbon stream or by a separate feed. The methanol is preferably fed at the upstream end of the reactor to inhibit oligomerization of the olefins and to preferentially react with more reactive isoolefins to form ethers.

The alcohol, e.g., methanol may be and is preferably present in a stoichiometric amount of the isoolefin present although an excess of up to 10%, may be desirable. In addition slightly less than a stoichiometric amount may be employed. It should be appreciated that the skilled chemist will optimize the proportions and precise conditions for each particular piece of equipment and variation in catalyst, once the basic invention is comprehended. The alcohols employed are those having 1 to 6 carbon atoms. Preferred are those having one hydroxyl group. Preferred alcohols include methanol, ethanol, propanol, n-butanol, tertiary butanol, 1-pentanol, 2-pentanol, 3-pentanol, 1-hexanol, 2-hexanol, 3-hexanol, cyclopentanol and hexanol. A preferred grouping of alcohols are those having 1 to 4 carbon atoms and one hydroxyl group.

The alcohols may be used alone or in mixtures of any proportion to produce highly complex ether products having unique properties as octane improvers for gasoline or as solvents.

The reaction in the fixed bed is primarily a liquid phase reaction, but unlike all other known liquid oligomerizations and etherifications reactions carried out in this manner, no attempt is made in the present process to maintain a completely liquid phase. Since the reaction is exothermic, the pressure in the reactor is adjusted to maintain the desired temperature which allows some portion of the material to be vaporized. The reactor may be said to run in a quasi-isothermal manner.

EXAMPLE 1

Figure 1:
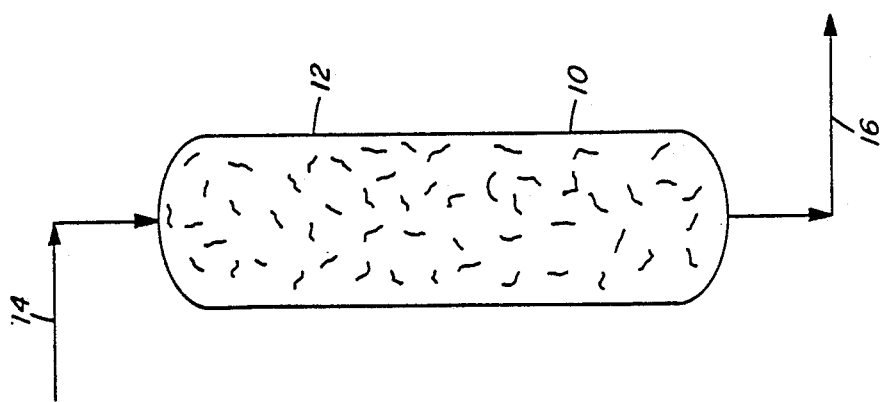
FIG. 1 is a simple reactor operated in a quasi-isothermal manner.

Referring to FIG. 1, a simple reactor 10, packed with acidic cation exchange resin catalyst 12 is shown. The reactor was pilot plant size and contained a 10 foot by 2 inch diameter bed of Amberlyst 15 Beads.

The feed was of refinery $C_4$ cut admixed with methanol and entered the reactor via line 14. The feed had been preheated to 138° F., and flowed through the resin bed and exited via line 16. The feed entering the reactor was in liquid phase and the product exiting was partially vaporized. The conditions and results of this run are summarized in TABLE I. Conversion of isobutene 89.7%.

The recovered stream 16 would normally be subjected to further treatment, by way of fractionation to separate the unreacted $C_4$ from the ether and to recover the unreacted methanol. The product stream 16 can go directly into a distillation column (not shown) where the heat of the reaction is utilized in the distillation.

EXAMPLES 2 and 3

In FIG. 2 modification of the simple procedure of FIG. 1 is illustrated. The feed, a refinery $C_4$ stream, enters heat exchangers 50 via line 60 where it indirectly contacts product from reactor 52 which enters the heat exchanger via 54. Once the reaction is started the product exiting the reactor is at a higher temperature than the feed and is used to heat feed entering the reactor via line 56. As in FIG. 1, the feed is a mixture of the $C_4$'s and methanol. After the indirect contact of the reaction product and feed in the heat exchange 50 the cooled product exits via line 58.

Operated in this manner the feed to reactor is at a temperature near the exotherm, hence the reactor is operating under near adiabatic conditions.

The net heat of reaction of the system is the difference between the temperature of the feed into the system and the product out of the system, i.e., 45° F., which is about the same as for the simple system illustrated in FIG. 1 (since the feeds are similar). The conditions and results of the two runs with two different C4 feeds are illustrated in Table II using the system of FIG. 2. It should be noted that the feed of Example 3 contained a higher isobutene content than Example 1. Since the pressure was the same for both examples the exotherm for Example 3 was higher. In order to have reduced the temperature in Example 3, the pressure would have needed to have been reduced, since the composition in the reactor had changed.

In either embodiment (FIG. 1 or FIG. 2) the product stream may be passed to a second or subsequent quasi-isothermal reactor and the process repeated. This would be expedient when the isoalkene is greater than about 30% of the feed, since conversion would be low on a per pass basis. Also, as shown in FIG. 2, the product stream 58 may be fed to a distillation tower 62 where the ether product is recovered as a bottoms 64 and unreacted feed stream components and methanol recovered as overhead 66.

Alternatively, tower 62 may be catalytic distillation tower where the residual isoalkene is reacted with residual methanol (or added methanol to produce extremely high conversions of the isoalkene in a single pass through the system (e.g. 95%+). The packing in a catalytic distillation column is described in the above noted patents, but briefly, it has been found that placing the resin beads into a plurality of pockets in a cloth belt, which is supported in the distillation column reactor by open mesh knitted stainless steel wire by twisting the two together, allows the requisite flows, prevents loss of catalyst, allows for the normal swelling of the beads and prevents the breakage of the beads through mechanical attribution.

The cloth may be of any material which is not attacked by the hydrocarbon feed or products under the conditions of the reaction. Cotton or linen are useful, but fiber glass cloth or "Teflon" cloth are preferred. A preferred catalyst system comprises a plurality of closed cloth pockets arranged and supported in said distillation column reactor and supported in said distillation column reactor by wire mesh intimately associated therewith.

The particular catalytic material may be a powder, small irregular fragments or chunks, small beads and the like. The particular form of the catalytic material in the cloth pockets is not critical, so long as sufficient surface area is provided to allow a reasonable reaction rate. This sizing of catalyst particles can be best determined for each catalytic material (since the porosity or available internal surface area will vary for different materials, and, of course, affects the activity of the catalytic material).

For the present oligomerizations and etherifications, the catalyst is the same type, an acidic cation exchanged resin, used in the continuous bed reactors.

It should be appreciated that the same mechanism of allowing excess heat of reaction to merely create boil up has been employed in both the continuous bed rectors and in the catalytic distillation. Although as noted above, continuous bed reactors have been disclosed to operate for different process in a quasiisothermal manner the operation of a liquid phase etherification in this manner is in direct conflict with all of art on the subject.

In the three examples of the present invention given here approximately 30% of the feed in the continuous bed quasiisothermal reactor was vaporized. In Examples 2 and 3 the product 54 leaving the heat exchanger was all liquid, however, in some operations according to the present invention, depending on the temperature and composition of stream 54, a portion may still be in the vapor state.

The heat exchanger 62 should be sized, such that an amount of heat equal to the heat of reaction in reactor 52 is allowed to pass through, otherwise the heat in the reactor will build up. An alternative means is to provide a by pass, shown by dashed line 55 whereby a portion of the effluent from the reactor is by passed around the heat exchanger to obtain the same result.

In the oligomerization, just as in the etherification, the tertiary olefins are more reactive and tend to form oligomers, primarily dimers, e.g., diisobutene, some higher oligomers and some codimers with normal olefins. The oligomerizations are run under the same general conditions as the etherifications with the oligomer products being the heavier component of the product stream. In fact, it may be desirable in some operations to switch between the two reactions, by adding or withholding the alcohol as desired.

TABLE I

|  | Line 14 | | Line 16 | |
| --- | --- | --- | --- | --- |
| Conditions | | | | |
| Temp., °F. | 138 | | 185 | |
| Press., psig | — | | 150 | |
| LHSV 11.9 | | | | |
|  | lbs/hr | wt % | lbs/hr | wt % |
| Composition | | | | |
| Isobutene | 15.6 | 14.6 | 1.6 | 1.5 |
| Other C4's | 79.4 | 74.2 | 79.4 | 74.2 |
| Methanol | 12.0 | 11.2 | 4.0 | 3.7 |
| MTBE | — | — | 22.0 | 20.6 |
| Conversion of isobutene | 89.7% | | | |

TABLE II

| Example 2 | | | | | + Example 3 | | | | |
| --- | --- | --- | --- | --- | --- | --- | --- | --- | --- |
| Conditions | Line 60 | Line 56 | Line 54 | Line 58 | + | Line 60 | Line 56 | Line 54 | Line 58 |
| Temp., °F. | 90 | 170 | 185 | 135 | + | 90 | 186 | 201 | 156 |
| Press., psig | — | — | 150 | 150 | + | — | — | 150 | 150 |
| LHSV 10.2 | | | | | | | | | |
| Composition | lbs/hr | wt. % | lbs/hr | wt. % | + | lbs/hr | wt. % | lbs/hr | wt. % |
| Isobutene | 13.1 | 14.2 | 0.9 | 1.0 | + | 21.8 | 20.4 | 3.8 | 3.6 |
| Other C4's | 66.9 | 72.7 | 66.9 | 72.7 | + | 68.2 | 63.7 | 68.2 | 63.7 |
| Methanol | 12.0 | 13.1 | 5.0 | 5.4 | + | 17.0 | 15.9 | 6.7 | 6.3 |
| MTBE | — | — | 19.2 | 20.9 | + | — | — | 28.3 | 26.4 |
| Conversion of isobuten - 93.1% | | | | | + Conversion of isobutene - 82.6% | | | | |

What is claimed is:

1. An improvement in the process of the exothermic, liquid phase reaction of $C_4$ or $C_5$ olefins with themselves to form oligomers thereof by contacting a downflow stream containing up to 60 weight percent of said olefins with a vertical fixed bed catalyst comprising an acid cation exchange resin at a temperature in the range of 120° F. to 300° F. in a reactor to form a reaction mixture containing oligomers, wherein the improvement comprises the operation of said reactor at a pressure to maintain said reaction mixture in said reactor at its boiling point within the range of 120° F. to 300° F. whereby at least a portion but less than all of said reaction mixture is vaporized, said reaction occurring in said liquid phase portion, and all of said reaction mixture is recovered as a single stream exiting through the lower end of the reactor.

2. The process according to claim 1 wherein a predominantly $C_4$ hydrocarbon stream from 1 to 60 weight percent isobutene is contacted with said fixed bed catalyst.

3. The process according to claim 2 wherein the pressure in the reactor is in the range of 0 to 400 psig and the LHSV of said stream is in the range of 5 to 20.

4. The process according to claim 3 wherein mixture contains unreacted $C_4$ hydrocarbon and a predominant of diisobutene.

5. The process according to claim 4 wherein said stream is preheated by indirect heat exchange contact with the reaction mixture from said reactor.

6. The process according to claim 1 wherein a predominantly $C_5$ hydrocarbon stream containing from 1 to 60 weight percent isoamylene is contacted with said fixed bed catalyst.

7. The process according to claim 6 wherein the pressure in the reactor is in the range of 0 to 400 psig and the LHSV of said stream is in the range of 5 to 20.

8. The process according to claim 7 wherein said reaction mixture contains unreacted $C_5$ hydrocarbon and a predominent amount of dimers of isoamylene.

9. The process according to claim 8 wherein said stream is preheated by indirect heat exchange contact with the reaction mixture from said reactor.

10. The process according to claim 1 wherein said stream is preheated prior to contact with said catalyst.

11. The process according to claim 1 wherein said reaction mixture is passed to a distillation column reactor containing an acid cation exchange resin in a plurality of pockets in a cloth belt supported in said distillation column reactor by open mesh knitted stainless steel wire to further react said isoolefins with themselves to form oligomers thereof.

* * * * *